United States Patent [19]

Piatak, Jr. et al.

[11] Patent Number: 4,948,729
[45] Date of Patent: Aug. 14, 1990

[54] PRODUCTION OF SOLUBLE RECOMBINANT PROTEINS

[75] Inventors: Michael Piatak, Jr., Walnut Creek; Walter J. Laird, Pinole; Julie A. Lane, Oakland, all of Calif.

[73] Assignee: Cetus Corporation, Emeryville, Calif.

[21] Appl. No.: 171,132

[22] Filed: Mar. 17, 1988

Related U.S. Application Data

[63] Continuation-in-part of Ser. No. 715,933, Mar. 25, 1985, abandoned.

[51] Int. Cl.$^5$ .............. C12P 21/00; C12N 15/00; C12N 1/20; C07H 21/04
[52] U.S. Cl. .................. 436/68; 435/172.1; 435/172.3; 435/252.3; 435/320; 536/27; 935/11; 935/46; 935/72
[58] Field of Search .............. 435/68, 70, 71, 91, 435/172.3, 172.1, 243, 252.3, 252.31–252.35, 849; 536/27; 935/10, 11, 29, 40, 41, 72, 73, 46

[56] References Cited

PUBLICATIONS

Michaelis et al., "In vitro construction and characterization of phoA–lacZ gene fusions in Escherichia coli", J. Bacteriol. 154:356.

Roberts et al., "A general method for maximizing the expression of a cloned gene", Proc. Natl. Acad. Sci. USA 76:760 (1979).

*Genes,* Lewin, 1983, John Wiley & Sons, New York, pp. 679 and 683.

Normark et al., *Ann. Rev. Genet.,* 17:499–525 (1983).

*Primary Examiner*—James Martinell
*Attorney, Agent, or Firm*—Gregory J. Giotta; Albert P. Halluin

[57] ABSTRACT

A system for expression of coding sequences for desired heterologous proteins in procaryotic hosts whereby the protein is produced intracellularly in soluble, biologically active form, is disclosed. The expression is obtained by ligation of the coding sequence downstream of, and proximally to, but out of reading frame with, the terminated leader encoding sequence for a secreted bacterial protein, such as alkaline phosphatase. The resultant proteins are influenced by the leader sequence codons to effect the desired three-dimensional conformation, but not to effect secretion.

8 Claims, 8 Drawing Sheets

```
       PHOA                           RICIN A
G T G A C A A A G G C G|G C A T T C C C C A A A C A A T A C C C A A T T ---
C A C T G T T T C C G C|C G T A A G G G G T T T G T T A T G G G T T A A ---
V A L T H R L Y S A L A A L A P H E P R O L Y S G L N T Y R P R O I L E ---
                      ↑   ↑
                        ?
```

(A) FUSION - pRAP 218

```
       PHOA          RICIN A
G T G A C A A A G G C|G A T C T T C C C C A A A C A A ---
C A C T G T T T C C G C|T A G A A G G G G T T T G T T ---
V A L T H R L Y S A L A I L E P H E P R O L Y S G L N ---
                       ↑
```

(B) FUSION - pRAP 2210

```
  PHOA ──────▶
V A L T H R L Y S A L A I L E S E R L E U T E R
G T G A C A A A G G|C G A T A A G C T T A T G A T A T T C C C C A A A ---
C A C T G T T T C C G C|T A T T C G A A T A C T A T A A G G G T T T ---
                    *                 ─── ─── ─── ─── ───
                                           M E T I L E P H E P R O L Y S
                                           |────▶ RICIN A
```

(C) FUSION - pRAP 229

```
G T G A C A A A G G|C G C C G A C A C C A G A A A T G ---
C A C T G T T T C C G C|G G C T G T G G T C T T T A C ---
V A L T H R L Y S A L A P R O T H R P R O G L U M E T
   (LEADER)              ↑   (NATIVE PROTEIN)
```

REFERENCE - MODIFIED PHOA SEQUENCE (CONTAINING NarI SITE)

↑ = POTENTIAL OR EXPECTED PROCESSING SITE

FIG. 8

```
                                                              (HindIII)
                                  (1) ccaagaattgctgcaaaagcttatgaaaccggg
TCTTCCTCAGCTGCTCACTTTCCAATAAAATTCCAAGAATTGCTGCAATCAAAGATGAAACCGGGAGGAAATACT
                                                        METLysProGlyGlyAsnThr BamH1               (2) ctttcacattagag
ATTGTAATATGGATGTATGCAGTGGCAACATGGCTTTGTTTTGGATCCACCTCAGGGTGGTCTTTCACATTAGAG
IleValIleTrpMETTyrAlaValAlaThrTrpLeuCysPheGlySerThrSerGlyTrpSerPheThrLeuGlu
(HindIIIMET)                                  --- <------(leader) <-----
                aagcttatgatattcccaaac
GATAACAACATATTCCCCAAACAATACCCAATTATAAACTTTACCACAGCGGGTGCCACTGTGCAAAGCTACACA
AspAsnAsnIlePheProLysGlnTyrProIleIleAsnPheThrThrAlaGlyAlaThrValGlnSerTyrThr
RTA- <-------IlePheProLysGlnTyrProIleIleAsnPheThrThrAlaGlyAlaThrValGlnSerTyrThr AACTTTATCAGAGCTGTTCGCGGTCGTTTAACAACTGGAGCTGATGTGAGACATGAAATACCAGTGTTGCCAAAC
AsnPheIleArgAlaValArgGlyArgLeuThrThrGlyAlaAspValArgHisGluIleProValLeuProAsn
RTA-AsnPheIleArgAlaValArgGlyArgLeuThrThrGlyAlaAspValArgHisGluIleProValLeuProAsn AGAGTTGGTTTGCCTATAAACCAACGGTTTATTTTAGTTGAACTCTCAAATCATGCAGAGCTTTCTGTTACATTA
ArgValGlyLeuProIleAsnGlnArgPheIleLeuValGluLeuSerAsnHisAlaGluLeuSerValThrLeu
RTA-ArgValGlyLeuProIleAsnGlnArgPheIleLeuValGluLeuGlnAsnHisAlaGluIleSerValThrLeu GCGCTGGATGTCACCAATGCATATGTGGTAGGCTACCGTGCTGGAAATAGCGCATATTTCTTTCATCCTGACAAT
AlaLeuAspValThrAsnAlaTyrValValGlyTyrArgAlaGlyAsnSerAlaTyrPhePheHisProAspAsn
RTA-AlaLeuSerValThrAsnAlaTyrValValGlyTyrArgAlaGlyAsnSerAlaTyrPhePheHisProAspAsn CAGGAAGATGCAGAAGCAATCACTCATCTTTTCACTGATGTTCAAAATCGATATACATTCGCCTTTGGTGGTAAT
GlnGluAspAlaGluAlaIleThrHisLeuPheThrAspValGlnAsnArgTyrThrPheAlaPheGlyGlyAsn
RTA-GlnGluAspAlaGluAlaIleThrHisLeuPheThrAspValGlnAsnArgTyrThrPheAlaPheGlyGlyAsn TATGATAGACTTGAACAACTTGCTGGTAATCTGAGAGAAAATATCGAGTTGGGAAATGGTCCACTAGAGGAGGCT
TyrAspArgLeuGluGlnLeuAlaGlyAsnLeuArgGluAsnIleGluLeuGlyAsnGlyProLeuGluGluAla
RTA-TyrAspArgLeuGluGlnLeuAlaGlyAsnLeuArgGluAsnIleGluLeuGlyAsnGlyProLeuGluGluAla ATCTCAGCGCTTTATTATTACAGTACTGGTGGCACTCAGCTTCCAACTCTGGCTCGTTCCTTTATAATTTGCATC
IleSerAlaLeuTyrTyrTyrSerThrGlyGlyThrGlnLeuProThrLeuAlaArgSerPheIleIleCysIle
RTA-IleSerAlaLeuTyrTyrTyrSerThrGlyGlyThrGlnLeuProThrLeuAlaArgSerPheIleIleCysIle CAAATGATTTCAGAAGCAGCAAGATTCCAATATATTGAGGGAGAAATGCGCACGAGAATTAGGTACAACCGGAGA
GlnMETIleSerGluAlaAlaArgPheGlnTyrIleGluGlyGluMETArgThrArgIleArgTyrAsnArgArg
RTA-GlnMetIleSerGluAlaAlaArgPheGlnTyrIleGluGlyGluMetArgThrArgIleArgTyrAsnArgArg TCTGCACCAGATCCTAGCGTAATTACACTTGAGAATAGTTGGGGGAGACTTTCCACTGCAATTCAAGAGTCTAAC
SerAlaProAspProSerValIleThrLeuGluAsnSerTrpGlyArgLeuSerThrAlaIleGlnGluSerAsn
RTA-SerAlaProAspProSerValIleThrLeuGluAsnSerTrpGlyArgLeuSerThrAlaIleGlnGluSerAsn CAAGGAGCCTTTGCTAGTCCAATTCAACTGCAAAGACGTAATGGTTCCAAATTCAGTGTGTACGATGTGAGTATA
GlnGlyAlaPheAlaSerProIleGlnLeuGlnArgArgAsnGlySerLysPheSerValTyrAspValSerIle
RTA-GlnGlyAlaPheAlaSerProIleGlnLeuGlnArg   AspGlySerLysPheSerValTyrAspValSerIle
                                                                        (TER)
                                (3) cacagttttaattgcttataagg
TTAATCCCTATCATAGCTCTCATGGTGTATAGATGCGCACCTCCACCATCGTCACAGTTTTCTTTGCTTATAAGG
LeuIleProIleIleAlaLeuMETValTyrArgCysAlaProProProSerSerGlnPheSerLeuLeuIleArg
RTA-LeuLeuProIleIleAla   MetValTyrArgCysAlaProProProSerSerGlnPhe( <--A-chain)

BamH1
CCAGTGGTACCAAATTTTAATGCTGATGTTTGTATGGATCCTGAGCCCATAGTGCGTATCGTAGGTCGAAATGGT
ProValValProAsnPheAsnAlaAspValCysMETAspProGluProIleValArgIleValGlyArgAsnGly
RTB-       (B-chain->)AlaAspValCysMetAspProGluProIleValArgIleValGlyArgAsnGly
```

PRODUCTION OF SOLUBLE RECOMBINANT PROTEINS

This application is a continuation-in-part of application Ser. No. 715,933, filed 3/25/85, now abandoned.

TECHNICAL FIELD

The invention relates to production of heterologous proteins using recombinant techniques. More specifically, the invention relates to utilizing a bacterial leader sequence to obtain biologically active, soluble forms of heterologous proteins produced intracellularly in procaryotes

BACKGROUND ART

It has, for some time been recognized that while the production of a desired amino acid sequence in procaryotic hosts can be effected by transforming procaryotes with expression vectors containing the appropriate coding sequences under control of procaryotic-compatible promoters, and, desirably, terminators, the resulting proteins may lack the three-dimensional configuration of corresponding proteins produced in their native hosts. Typically, mammalian or other heterologous proteins produced by procaryotic hosts are synthesized in relatively insoluble form, often in the form of particles visible under microscopic examination, said particles variously referred to as "inclusion" or "refractile" bodies.

These insoluble proteins may be successfully identified by immunoprecipitation with antibodies raised against the native forms of the protein but may nevertheless be deficient in their biological activity, presumably due to incorrect folding (see, for example, EPO Publication 114,506, published 8 Jan. 1984), It has been assumed that some of these problems could be eliminated by causing the protein to be secreted either into the periplasm, in the case of gram-negative organisms, or into the medium in the case of gram-positives, presumably because transport through the cellular membrane would result in the proper folding. Indeed, in some instances it has been found possible to prepare soluble, biologically active recombinant proteins using this approach.

Particular instances in which standard techniques of bacterial expression for heterologous proteins have resulted in products which are relatively insoluble and not properly biologically active include standard methods for producing interleukin-2 (IL-2), β-interferon (IFN-β), and ricin A. In the case of ricin A, material obtained by using expression vectors which are plasmids placing the ricin A coding sequence under the control of the trp or $P_L$ promoter, standard "work horse" promoters used in bacterial expression, results in production of a ricin A product which cannot readily be solubilized in the absence of detergents, and which, therefore, does not exhibit cytotoxic activity when conjugated with antibodies to obtain immunoconjugates. Indeed, such immunoconjugates are not cytotoxic even in vitro. The ability of the recombinant ricin A to immunoprecipitate with antibodies raised against the native material is retained, as is the enzymatic ability of the ricin A to inhibit protein synthesis in the standard rabbit reticulocyte assay. It is, therefore, concluded that methods for expression of ricin A using these approaches results in a product which requires additional manipulations to configure the molecule in a three-dimensional array that will enable it to function as a portion of an immunotoxin. Purification procedures cannot readily be applied to the material which has been solubilized by the aid of detergent, and, indeed, it has not proved possible to remove the detergent from the solubilizing solution and retain this material in solution.

By using the expression system of the invention, however, the recombinantly produced ricin A remains soluble in the sonicate from whole cells, and can readily be purified in the absence of detergent. Immunoconjugates prepared with the thus-purified ricin A are cytotoxic both in vivo and in vitro.

An attempt was made to utilize the alkaline phosphatase (phoA) leader and N-terminal sequence to effect secretion of a foreign polypeptide by Ohsuye, K., et al, *Nucleic Acids Res* (1983) 11:1283. The coding sequence for α-neoendorphin, a decapeptide hormone, was synthesized in vitro and ligated into vectors so as to produce fusion proteins of the endorphin with the ma)or portion of the alkaline phosphatase N-terminal sequence and leader. The resulting chimeric proteins were processed, but not transported into the periplasm.

It has now been found that the DNA sequence encoding certain bacterial leaders, notably the alkaline phosphatase-encoding leader, are capable of conferring solubility and biological activity characteristics on desired heterologous proteins independently of effecting passage through the membrane. This capacity of the bacterial leader sequence-encoding DNA may be utilized to provide directly the desired forms of proteins previously produced only in more intractable conformations.

DISCLOSURE OF THE INVENTION

The invention provides a means to obtain directly, and without supplementary refolding or reactivation procedures, the soluble biologically active forms of recombinant heterologous proteins. Proteins previously resistant to proper form production in procaryotic hosts, notably proteins such as ricin A chain, have been made in easily recoverable, biologically active form using the method of the invention. These proteins are produced intracellularly, and are obtained using sonicates of the host culture, but without special measures to confer solubility on the products.

Thus, in one aspect, the invention relates to a method for producing soluble, biologically active heterologous recombinant proteins, mainly ricin A, in procaryotes. The method employs DNA sequences wherein the coding sequence for the desired recombinant protein. Preceded by an ATG start codon, is placed downstream of, and proximal to the coding sequence for the appropriate bacterial leader, but out of reading frame with the leader. The leader is terminated by a stop codon proximal to the ATG. Suitable bacterial promoters and positive retroregulator sequences are also included in vectors effecting expression of the coding sequence.

Accordingly, other aspects of the invention include the vectors useful in the method of the invention, procaryotic host cells transformed with these vectors, and proteins produced using them. A specific embodiment of these aspects of the invention involving ricin A toxin is particularly significant, as it represents the first time that it has been possible to obtain immediately soluble, biologically active recombinant ricin A.

BRIEF DESCRIPTION OF THE DRAWINGS

FIG. 1 shows the 5' sequences of the phoA operon, and modification to place a NarI site at the C-terminus of the leader.

FIG. 5 shows the junction regions of the plasmids illustrated in FIGS. 3 and 4.

FIG. 8 shows the coding sequence and deduced amino acid sequence for the ricin A encoding insert of pRA123.

MODES OF CARRYING OUT THE INVENTION

A. Definitions

Figure 2:
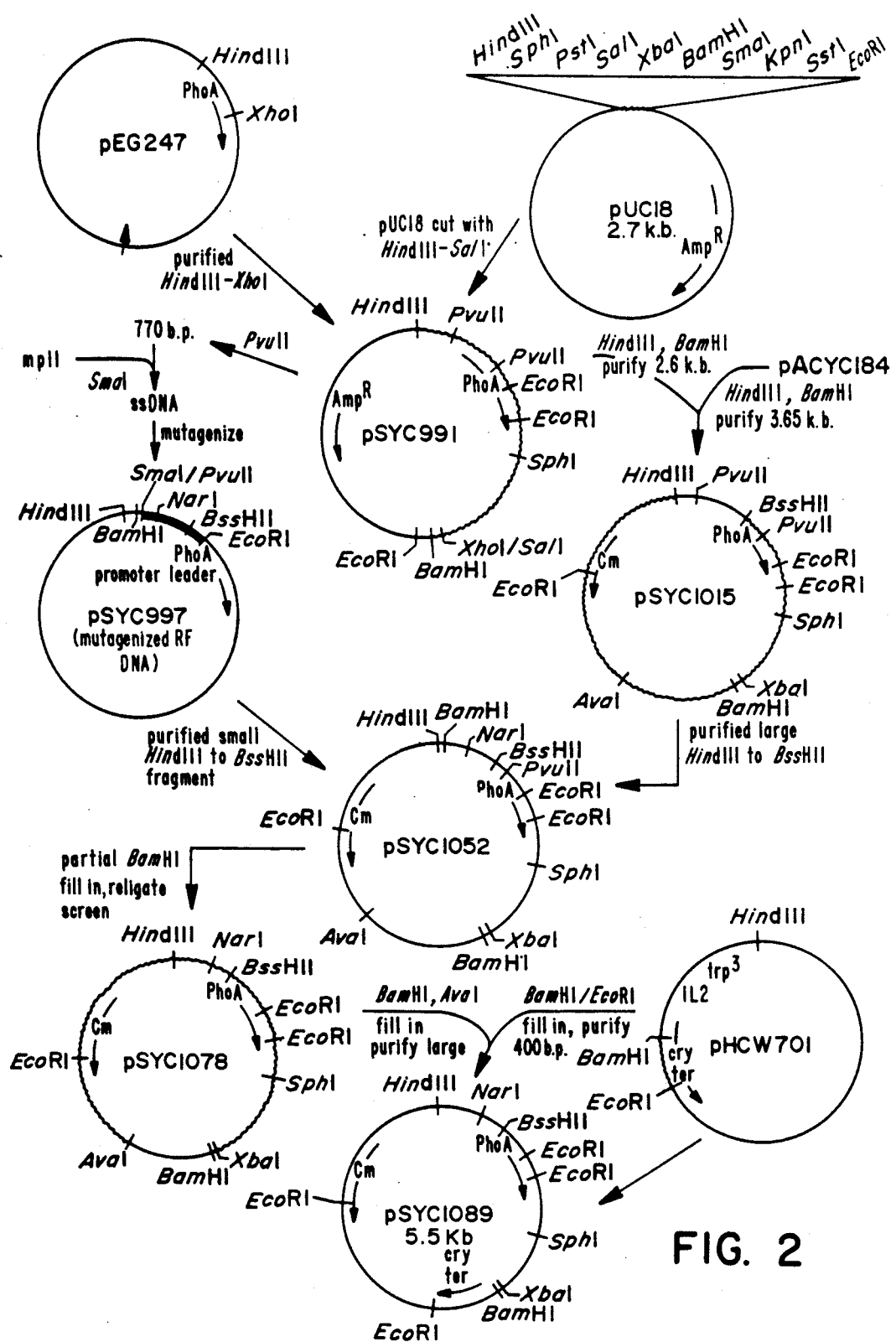
FIG. 2 shows the construction of pSYC1089, a host vector for expression of the proteins of the Invention.
Figure 3:
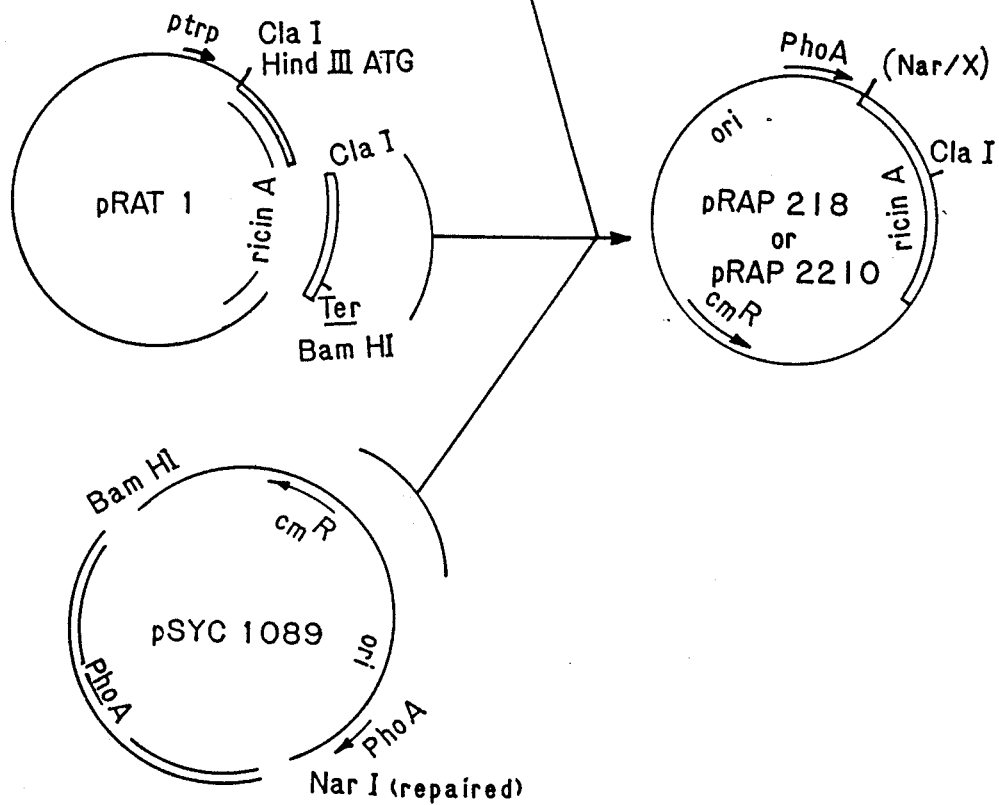
FIG. 3 shows the construction of pRAP2210 and pRAP218.
Figure 4:
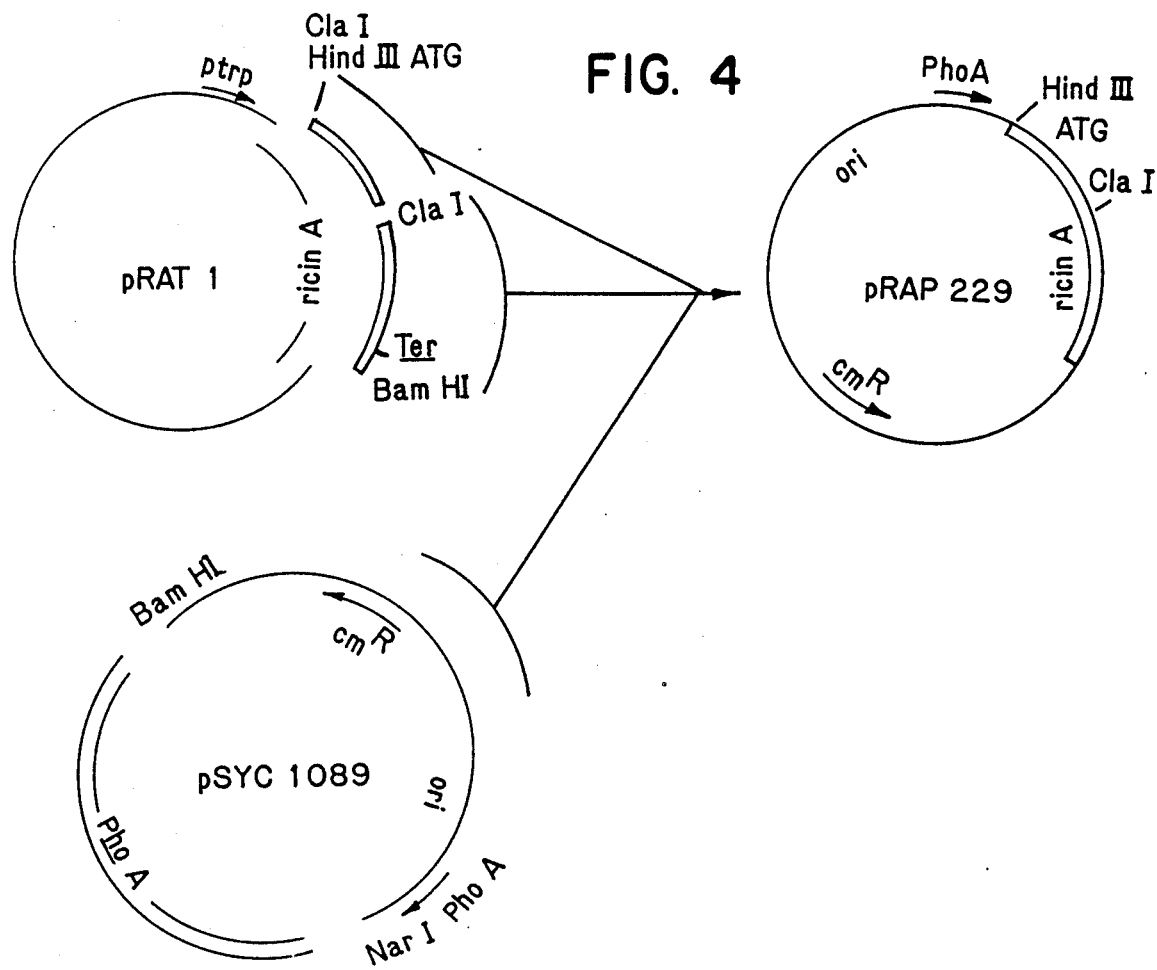
FIG. 4 shows the construction of pRAP229.
Figure 6:
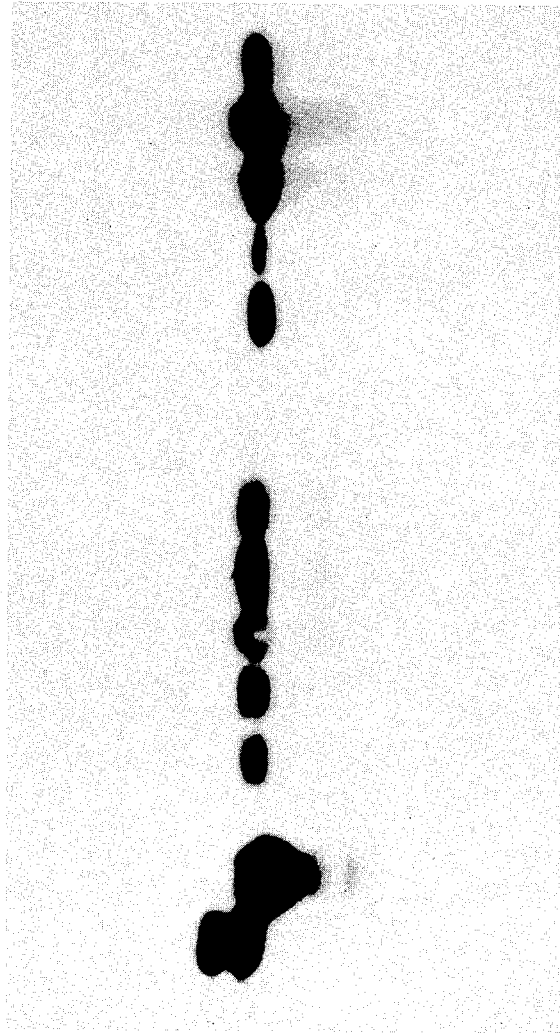
FIG. 6 shows the results of Western blots obtained using extracts of *E. coli* transformed with pRAP218 and pRAP229.
Figure 7:
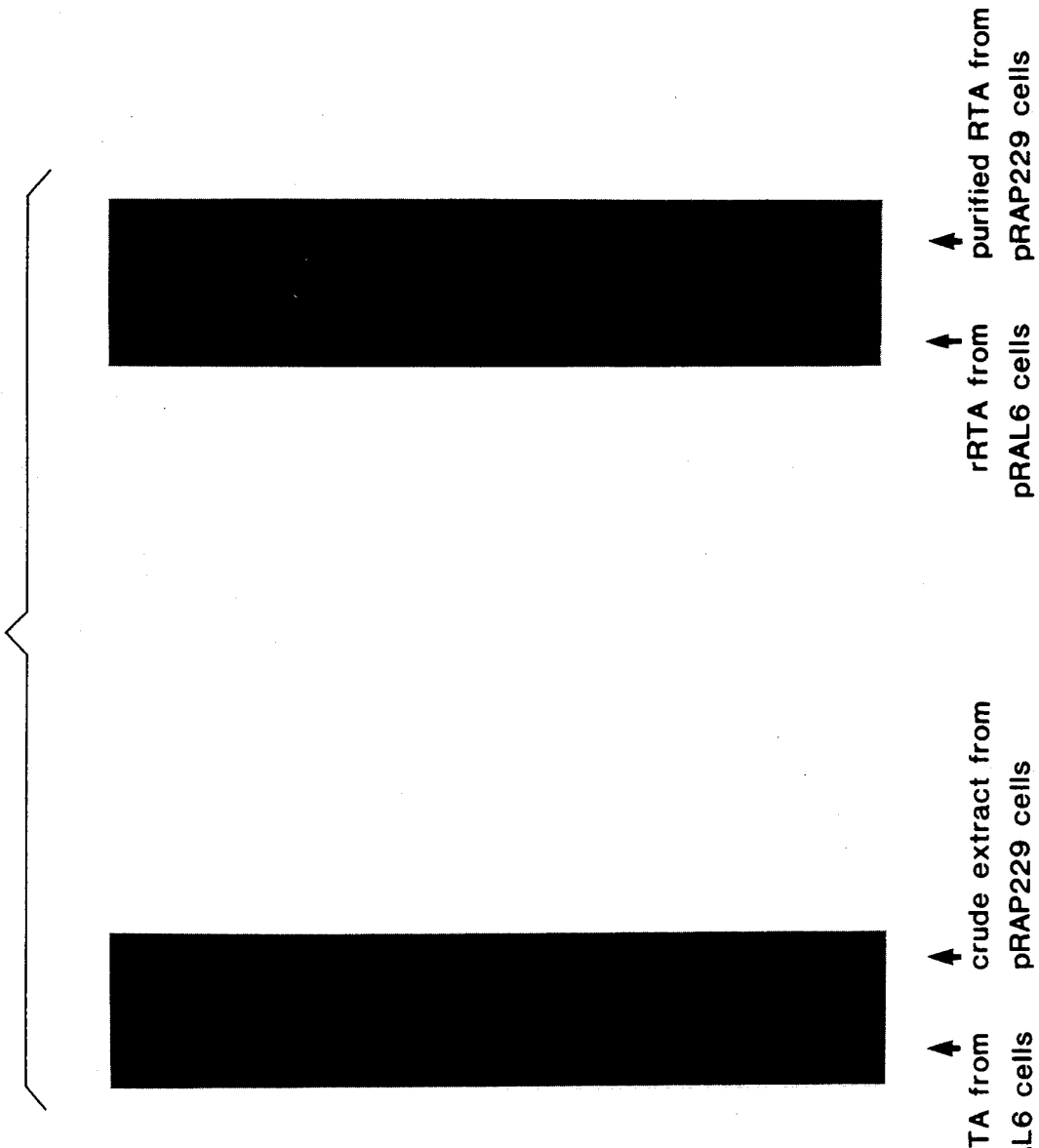
FIG. 7 shows comparative SDS-gels obtained from crude sonicate of pRAP229-transformed cells and from purified ricin A.

As used herein, "soluble" refers to a protein which remains in the supernatant after centrifugation for 30 min at 100,000 ×x g in aqueous buffer under physiologically isotonic conditions, for example, 0.14 M sodium chloride or sucrose, at a protein concentration of as much as 10 mg/ml. These conditions specifically, relate to the absence of detergents or other denaturants in effective concentrations such as guanidine or urea.

"Biologically active" refers to retaining the enzymatic and other biological behavior which typifies the function of the protein in its native state. The function of the protein in its native state may be assayable by several approaches. For example, the biological activity of ricin A refers to a series of three tests to show that the ricin A itself exhibits enzymatic activity, and, when coupled to a suitable cell binding agent, such as an antibody or fragment thereof, cytotoxicity in vitro, and/or cytotoxicity in vivo. "Enzymatic activity" refers to the ability of ricin A to inhibit protein synthesis in a rabbit reticulocyte in vitro translation system (a commercially available system obtainable e.g., from Bethesda Research Laboratories, Rockville, MD). Both in vitro and in vivo cytotoxicity are measured by specific cytotoxicity ("cytotoxic activity") tests showing the ability of the enzymatic protein inhibition of the ricin A to be directed against particular target cells when the ricin A is supplied to such cells in the form of an immunoconjugate. Immunoconjugates represent a class of materials which are prepared by covalently linking an antibody as a specific binding reagent to a cytotoxic or enzymatically active protein such as ricin A. The resulting immunotoxins then are, if active, capable of selectively killing cells against which the binding portion of the conjugate is directed. In order to be fully biologically active, ricin A, when conjugated to suitable antibodies, should be capable of selectively killing target cells either in cell culture or when the cells are implanted in, or resident in, an animal.

Typical recombinant ricin A preparations do not fulfill all three of these criteria. Typical preparations may be enzymatically active, but generally are not specifically cytotoxic by either in vivo or in vitro criteria. It is recognized that biological activity may be absent even when immunological cross-reactivity with antibodies raised against the specified protein remains.

The constructions of the invention, however, yield "biologically active" proteins. In the case of ricin A this refers to both enzymatic and cytotoxic activity.

As used herein, "ricin A" refers to a protein whose amino acid sequence is substantially similar to that of the ricin A peptide which is extractable from castor bean seeds. The ricin A of castor beans is approximately 265 amino acids in length and has a molecular weight of approximately 32,000 daltons. However, it is known that the precise sequence varies depending on the variety of bean.

"Substantially similar" means that the protein in question must be approximately the same length (arbitrarily within around 10%) but, more importantly, must retain the capacity of ricin A chain to interact with, and incapacitate, the 60S ribosome subunit. It is well known that some small alterations in protein sequence may be possible without disturbing the functional abilities of the protein molecule, although other modifications are totally destructive. It is not currently possible to predict with any assurance into which category a particular alteration will fall. The definition herein permits any modifications which are in the first category. Such alterations could result from chance mutations in the gene sequence or from deliberate alterations thereof.

Further, as is well known, protein sequences may be modified by post-translational processing such as association with other molecules, for example, glycosides, lipids, or such inorganic ions as phosphate. The ionization status will also vary depending on the pH of the medium, or the pH at which crystallization or precipitation of the isolated form occurs. Further, the presence of air may cause oxidation of labile groups, such as —SH. Included within the definition of ricin A are all such modifications of a particular primary structure–i.e., e.g., both glycosylated and non-glycosylated forms, neutral forms, acidic and basic salts, lipid or other associated peptide forms, side chain alterations due to oxidation or derivatization, and any other such modifications of an amino acid sequence which would be encoded by the same genetic codon sequence.

"Secretion" refers to transport through the cellular membrane. Whether or not the protein appears in the medium is dependent on the presence or absence of a cell wall; in the presence of cell walls the secreted protein will be found in the periplasm, in the absence of cell walls it will be in the medium.

"Alkaline phosphatase A" (phoA) refers to the alkaline phosphatase structural gene of *E. coli* K12 as, for example, disclosed by Kikuchi, Y., et al. *Nucleic Acids Res* (1981) 9:5671–5678. The structural gene is located at 8.5 minutes on the *E. coli* genetic map (Bachmann, B. J., et al, *Microbiol Rev* (1980) 44:1–56) and its native expression is relatively complex. However, the promoter and N-terminal regions have been sequenced (Kikuchi, Y., et al, (supra)) and the sequence of the signal peptide deduced (Inouye, H., et al, *J Bacteriol* (1982) 149:434–439). The definition herein encompasses not only the specific structural gene and portions thereof, but functional equivalents derived from other bacterial sources or synthesized in vitro. It is understood that minor modifications may be made in the nucleotide sequences without affecting functionality, and that sequences derived from different strains or species of procaryotic cells may, and indeed almost surely do, contain sequences not absolutely identical to that of the above-mentioned source. In addition, in connection with the invention herein, modifications have been made to this sequence to provide suitable restriction cleavage sites, wherein these modifications do not result in loss of functionality.

Figure 1:
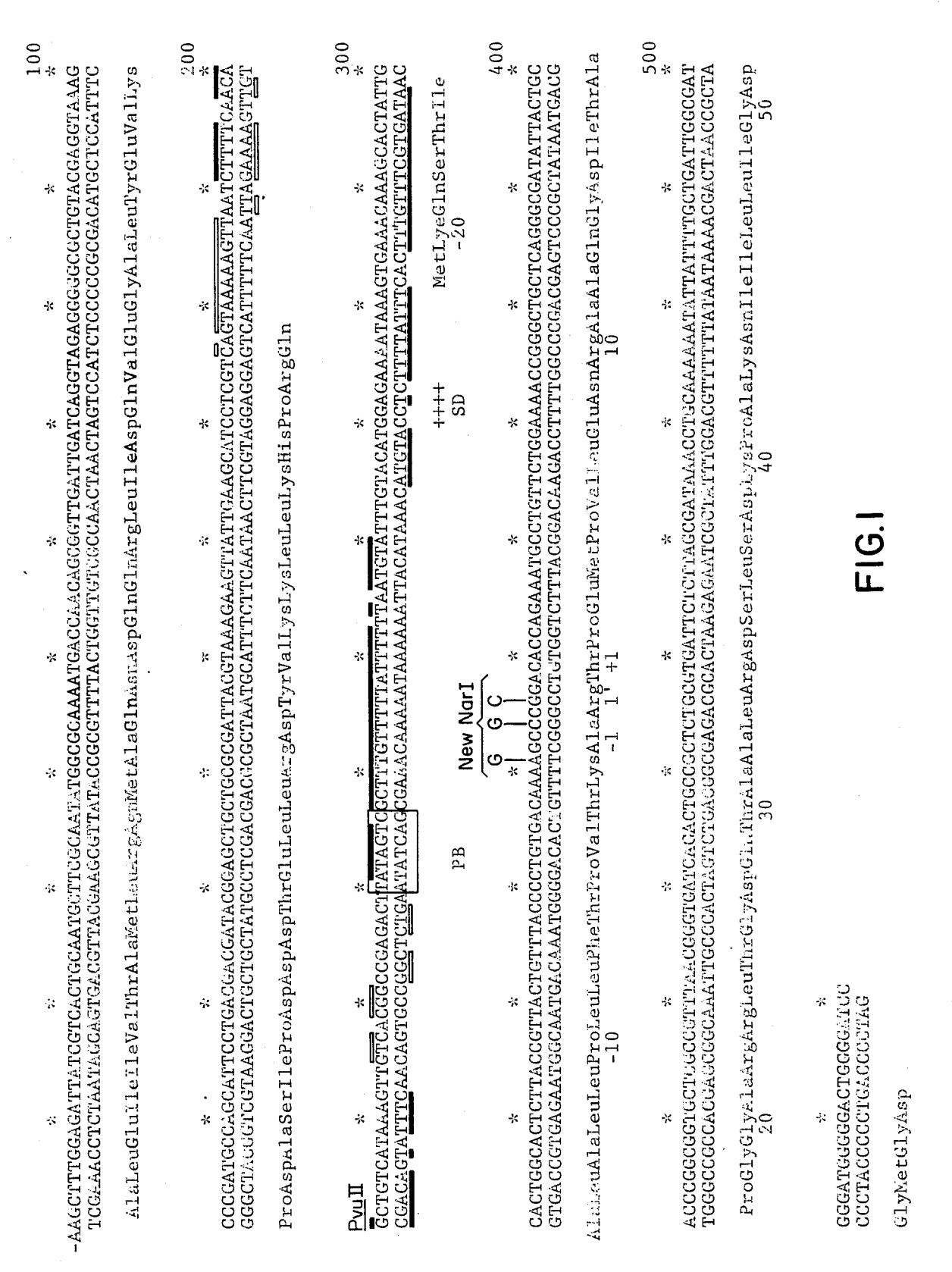

Of relevance to the present invention are the following regions of the alkaline phosphatase structural gene: the promoter, the ribosome binding site, the leader sequence, and the terminator or positive retroregulator sequence. The constructions exemplified below utilize the phoA upstream controls and leader, but substitute a *B. thuringiensis* crystal protein gene positive retroregulator for the phoA counterpart. The nucleotide sequence of the 520 bp fragment which includes the promoter, ribosome binding site, and signal are disclosed in Kikuchi, Y., (supra). The nucleotide sequence of the leader, modified to provide a NarI site is shown in FIG. 1. This modification permits coding sequences other than alkaline phosphatase to be substituted in reading frame with leader, and in that sense the leader is still functional. However, conversion to the NarI site prevents processing with respect to alkaline phosphatase itself since the codon for the N-terminal arginine of the alkaline phosphatase phosphatase sequence is now converted to a proline. Functionality with respect to inserted sequences is not impaired as this portion of the NarI site is eliminated in the junctions.

A "terminated" leader sequence refers to a leader peptide having a stop codon in reading frame proximal to its normal carboxy terminus. In the expression systems of the invention, the termination codon is also proximal to the ATG start codon of the desired heterologous protein. Accordingly, the leader or the desired "mature" protein may have slightly fewer or slightly more amino acids encoded in this junction region than their native counterparts.

"Operably linked" refers to juxtaposition wherein the functionality of the operably linked subjects are preserved. Thus, promoter operably linked to a coding sequence results in expression of the coding sequence under control of the promoter; desired protein operably linked to leader sequence refers to the protein disposed at the C-terminus of the leader. Positive retroregulator operably linked to a coding sequence aids in effective expression.

"Cells", "cell cultures", "host cells", "recombinant host cells" refer to subject cells for recombinant DNA manipulations. As would be apparent from the context, these cells may be candidates for, or resultants of, transfer of new DNA sequences according to recombinant techniques. Techniques which are suitable for DNA uptake by cells include, most prominently, in vitro transformation, however other techniques such as transduction or conjugation may also be used. The definition further includes the progeny of the cells directly referred to, It is understood that such progeny may not be precisely identical in DNA content to their parents, but such progeny are included in the definition so long as alterations due, for example, to accidental or deliberate mutation do not destroy the ability of the cells to exhibit the properties conferred by the DNA introduced, in a manner similar to that exhibited by their parents.

B. General Description

Placing the coding sequence for a subject protein into direct reading frame with the DNA encoding leader sequence of phoA, in order to form a putative fusion peptide wherein the leader sequence is the N-terminal portion of a leader/desired peptide chimera, may lead to varied results with respect to processing and secretion. As demonstrated in the illustrations set forth as controls below, ricin A sequences so disposed are not secreted. However, a substantial fraction of the chimeric proteins resulting from these in-frame fusions are processed, even though they appear to remain in intracellular locations. In any event, the processed and unprocessed forms of the intracellular ricin A proteins remain soluble, unlike the recombinant mature ricin A formed under control of the trp or $P_L$ promoters.

While reading frame, leader-chimeric, constructions for ricin A result in acceptable product, this result may be dependent on the amino acid sequence of ricin A and is not clearly generalizable to all proteins. However, using the constructions of the invention, not only ricin A, but protein sequences in general may be provided in soluble, biologically active form intracellularly.

While the mechanism for this success has not been delineated with precision, it is clear that the requirements for expression system construction include placing the leader-encoding sequence, in the illustration below, the terminated phoA leader sequence, immediately upstream of the desired protein encoding sequence, but in a mismatched reading frame, and providing an initiation codon for the subject protein to permit its independent translation. A reasonable hypothesis by which Applicant, of course, does not intend to be bound is that the independently translated protein whose production is reinitiated by the ATG is placed into proximity to the cellular membrane by the cotranscribed and proximally translated leader. In any event the cellular environment in which the translated desired product now finds itself is evidently no longer hostile to correct folding and processing to obtain appropriate biological activity.

In the expression system of the invention, the essential component is the terminated phoA leader-encoding sequence upstream of, proximal to, and out of frame with the desired coding sequence, wherein the desired coding sequence is initiated by an ATG codon. The two coding sequences must be, of course, provided with a compatible bacterial promoter which can conveniently be the phoA promoter already associated with the leader, but, of course, can be any compatible procaryotic promoter/ribosome binding site system. Additionally, production is improved in the presence of a positive retroregulator sequence which again, can either be the phoA positive retroregulator or, more advantageously the positive retroregulator sequences associated with the crystal protein of *B. thuringiensis* The positive retroregulator sequences of *B. thuringiensis* have been cloned into a pRBR322 derivative, pLW1, which is on deposit with the American Type Culture Collection under the terms of the Budapest Treaty and has accession number 39405. The expression systems of the invention are typically provided on bacterial transport vectors which include such standard elements as replicons and selectable markers. The nature of these accessory elements does not form part of the invention, but optimization of these additional elements in the vectors of the invention is understood to be a desirable complement thereto.

The vectors are then used to transform suitable procaryotic hosts, which are grown under conditions suitable for the particular host chosen, most frequently under conditions whereby the promoter placed in control of the expression system is suppressed. The production of the desired protein is then induced by providing conditions which effect expression under control of the chosen promoter and the production permitted to proceed for sufficient time to effect a desired accumulation of product. The protein product is then isolated by disrupting the cells, for example, by sonication or by mechanical means such as a French press, and the cellular debris removed. The protein produced by the invention system is then further purified using standard techniques known in the art as applied to freely soluble proteins. The solubility of the ricin A or other desired protein in the sonicate (once separated from the membrane or other associated materials) is shown by its ability to remain in the supernatant when the sonicate is subjected to centrifugation at high speed, $100,000 \times g$ for 30 minutes, to spin down insoluble proteins.

The importance of remaining soluble is particularly important for ricin A in the context of purification procedures and testing for specific cytotoxicity. One commonly used method to obtain solubilization of recombinant proteins is to take them up in the presence of a detergent, such as, for example, urea, guanidine hydrochloride, or SDS. The detergent in the solutions, however, interferes both with the purification processes and with biological activity tests. Removal of the detergent from the solubilizing medium in many instances, and in particular in the instance of ricin A, results in reprecipitation of the protein, thus making it incapable of efficient purification and also rendering immunoconjugates formed using this material inactive in cytotoxicity tests.

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. Many of the techniques utilized in the illustrative procedures of ¶D are as described in U.S. Ser. No. 653,515, filed 20 Sept. 1984, assigned to the same assignee and incorporated herein by reference. However, given below for convenience and as a guideline are some of those methods as well as modifications and improvements thereof, and additional procedures employed herein.

C.1. Hosts and Control Sequences

The invention vectors are suitable for procaryotic expression. Procaryotes most frequently are represented by various strains of *E. coli*, a gram-negative organism. However, other microbial strains may also be used, such as the gram-positive bacilli, for example *Bacillus subtilis*, various species of *Pseudomonas*, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al *Gene* (1977) 2:95, pBR322 contains genes for ampicillin and tetracycline resistance, and thus provides additional markers which can be either retained or destroyed in constructing the desired vector. Other commonly used vectors are from the pUC series which contain polylinkers for convenient insertion of desired DNA. Commonly used procaryotic control sequences which include promoters for transcription initiation. optionally with an operator, along with ribosome binding site sequences, are exemplified by such commonly used promoters as the β-lactamase (penicillinase) promoter system (Chang, et al, *Nature* (1977) 198:1056) and the tryptophan (trp) promoter system (Goeddel, et al *Nucleic Acids Res* (1980) 8:4057) and the lambda derived $P_L$ promoter and N-gene ribosome binding site (Shimatake, et al, *Nature* (1981) 292:128), which has been made useful as a portable control cassette, as set forth in copending application Ser. No. 578,133, filed 8 Feb. 1984 and assigned to the same assignee. In the instant case, the phoA promoter is illustrated. However, any available promoter system compatible with procaryotes can be used.

C.2 Transformations

For the procaryotic hosts used in the invention, the calcium treatment employing calcium chloride, as described by Cohen, S. N., *Proc Natl Acad Sci (USA)* (1972) 69:2110, or the $RbCl_2$ method described in Maniatis, et al, Molecular Cloning: *A Laboratory Manual* (1982) Cold Spring Harbor Press, p. 254 was used.

C.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol or by passing through a Bio-Gel P6 spin column, followed by lyophilization. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleoside triphosphates (dNTPs) using incubation times of about 15 to 25 min at 20° to 25° C. in 50 mM Tris pH 7.6, 5 mM $MgCl_2$, 10 mM DTT, and 50 μM each dNTP. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated and/or followed by passing through a Bio-Gel P6 spin column.

Treatment with S1 nuclease under appropriate conditions results in rapid hydrolysis of any single-stranded portion of DNA and slow hydrolysis of double-stranded portions commencing at the ends. S1 nuclease hydrolyses are typically conducted in a buffer which is 15 mM sodium acetate, pH 4.5, 300 mM NaCl, and 1 mM ZnSO4, using approximately 200 units per μl of S1 nuclease. Ordinarily 50–100 units of S1 nuclease is used to hydrolyze approximately 10 μg of DNA.

Synthetic oligonucleotides are prepared by the triester method of Matteucci, et al (*J Am Chem Soc* (1981) 103:3185) or using commercially available automated oligonucleotide synthesizers. Kinasing of single strands prior to annealing or for labeling may be achieved using an excess, e.g., approximately 10 units of polynucleotide kinase to 0.1 nmole substrate in the presence of 50 mM Tris, pH 7.6, 5 mM MgCl2, 10 mM dithiothreitol, 1–2 mM ATP, 1.7 pmoles γ32P-ATP (2.9 mCi/mM), although variations are possible to obtain labeled material of various specific activities.

Ligations are performed in 15–30 μl volumes under the following standard conditions and temperatures: 50 mM Tris-HCl pH 7.6, 5 mM MgCl2, 10 mM DTT. 100 μg/ml BSA, and either 40 μM ATP. 0.01–0.02 (Weiss) units T4 DNA ligase at 5–12° C. (for "sticky end" ligation) or 1 mM ATP, 0.3–0.6 (Weiss) units T4 DNA ligase at 14–20° C. (for "blunt end" ligation).

In vector construction employing "vector fragments", the vector fragment is commonly treated with bacterial alkaline phosphatase (BAP) in order to remove the 5' phosphate and prevent religation of the vector. BAP digestions are conducted at pH 8.3 in approximately 50 mM Tris, in the presence of Mg+ using about 1 unit of BAP per μg of vector at 60° C. for about one hour. In order to recover the nucleic acid fragments, the preparation is extracted with phenol/-chloroform and ethanol precipitated and desalted by application to a Bio-Gel P6 spin column. Alternatively, religation can be prevented in vectors which have been double digested by additional restriction enzyme digestion of the unwanted fragments.

C 4. Site-Specific Mutagenesis

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. This temperature may be approximated as being 5–15° C. lower than the melting temperature (Tm) of the primer determined by the equation:

$$Tm = 7.2(ln[Na+]) + 0.41(\%G+C) + 81.2 - 500/(\text{length in nucleotides}).$$

Plaques which hybridize with the probe are then picked, cultured, and the DNA recovered.

In more detail approximately one pmol of the phage single-stranded DNA template is mixed with approximately 10 pmol of the synthetic oligonucleotide primer in 15 μl of 10 mM Tris. 10 mM MgCl2, 90 mM NaCl.

The mixture is heated to 67° for 3–5 minutes and then to 42° for 30 minutes. The mixture is then cooled on ice, and adjusted to contain each of the four dNTPs at 500 μM, dithiothreitol at 10 mM, and 3–5 units of Polymerase I (Klenow). The mixture is left at 0° C. for 5 minutes and then brought to 37° for 30 minutes. The Klenow is then inactivated for 5 minutes at 75°, and the mixture transformed into an appropriate host, such as DG98 (ATCC 39768) using 1 μl reaction mixture per 300 μl competent cells, which are grown with additional non-transformed cells on yeast extract-tryptone agar plates to obtain plaques.

Plates containing mutagenized plaques as well as control plates containing unmutagenized phage plaques, are chilled to 4° C. and phage plaques from each plate are transferred onto 2 nitrocellulose filter circles by layering a dry filter on the agar plate for 5 min for the first filter and 15 min for the second filter. The filters are then placed on thick filter papers soaked in 0.2 N NaOH, 1.5 M NaCl and 0.2% Triton X-100 for 5 min, and neutralized by layering onto filter papers soaked with 0.5 M Tris-HCl, pH 7.5, and 1.5 M NaCl for another 5 min. The filters are washed in a similar fashion on filters soaked in 2×SSC, dried and then baked in a vacuum oven at 80° C. for 2 hr. The duplicate filters are prehybridized at the determined hybridization temperature for 4 hr with 5–10 ml per filter of DNA prehybridization buffer (2×SSC, pH 7.0, 5×Denhardt's solution (polyvinyl-pyrrolidine, ficoll and bovin serum albumin, 1×=0.02% of each), 0.1% SDS, and 100 μg/ml of sheared denatured salmon sperm DNA). =P-labeled probes are prepared by kinasing the primer with labeled ATP. The filters are hybridized with about $10^6$ cpm/ml of $^{32}$P-labeled primer in 1–5 ml per filter of DNA hybridization buffer (prehybridization buffer minus the salmon sperm DNA) at the determined temperature for at least 8 hr.

The filters are washed once at room temperature for 10 min in 0.1% SDS. and 2×SSC followed by 2–3 washes in 2×SSC only until acceptable background levels of radioactivity are obtained. If necessary, higher temperatures may be employed. The filters are blotted to remove excess moisture and autoradiographed at −70° C. for 4 hr. The indicated mutagenized colonies are picked and inoculated into competent *E. coli* cultures to obtain quantities of the modified DNA. From these cultures, ssDNA is prepared from the supernatant and dsRF-DNA is prepared from the pellet.

C.5. Verification of Construction

Correct ligations for plasmid construction are confirmed by first transforming a suitable *E. coli* such as strain MM294 obtained from *E. coli* Genetic Stock Center, CGSC #6135, or other suitable host with the ligation mixture. Successful transformants are selected by ampicillin, tetracycline, chloramphenicol or other antibiotic resistance or using other markers depending on the mode of plasmid construction, as is understood in the art. Plasmids from the transformants are then prepared according to the method of Clewell, D. B., et al. Proc Natl Acad Sci (USA) (1969) 62:1159, optionally following chloramphenicol amplification (Clewell, D. B., J Bacteriol (1972) 110:667). The isolated DNA is analyzed by restriction and/or sequenced by the dideoxy method of Sanger, F., et al, proc Natl Acad Sci (USA) (1977) 74:5463 as further described by Messing, et al, Nucleic Acids Res (1981) 9:309, or by the method of Maxam, et al, *Methods in Enzymology* (1980) 65:499.

C.6. Western Blot Analysis

Analysis of cloned protein products by Western blot analysis is generally referenced by Bittner, M., et al, *Ann Biochem* (1980) 102:459–471, and Erlich, H.A., et al, *Infect Immun* (1983) 41:683–690. Proteins separated in SDS-polyacrylamide gels are transferred electrophoretically using commercially available apparatus (e.g., from BioRad Corp. or Hoeffer Scientific) to a suitable membrane support such as nitrocellulose, CNBr-activated paper, or one of a variety of commercially available derivatized nylon membranes (e.g., Gene Screen, Dupont/New England Nuclear or Pall Biodyne A, pall Corp.). Various methods for transfer and membrane reaction may be used and are supplied by the manufacturer of the apparatus and membranes. Specific cloned antigens are detected utilizing specific antisera, e.g., rabbit anti-ricin A sera, and a secondary detection system, for example, $^{125}I$ protein A (commercially available, New England Nuclear) or horseradish peroxidase conjugated anti-rabbit sera, developed appropriately to visualize the reactions.

C.7. Osmotic Shock

One indication that a protein produced in *E. coli* may reside in the periplasmic space and is thus "secreted" is that it can be released by an osmotic shock. This test was performed essentially as described by Nassal and Happel, *J Biol Chem* (1966) 241:3055–3062. Briefly pellets of induced cell cultures are suspended to a density of approximately $7 \times 10^9$ cells/ml in buffer containing 50 mM Tris, pH 7.4, 2.5 mM EDTA and 20% (w/v) sucrose, and kept at room temperature for 10 minutes. The cells are then pelleted and resuspended in ice-cold water and left on ice for 10 minutes. After centrifugation, the supernatant, herein referred to as the osmotic shockate, and the pellet, herein referred to as the osmotic cell pellet, are assayed by SDS-polyacrylamide gel electrophoresis and Western blot analysis.

C. 8. N-Terminal Peptide Sequencing

Commercially available systems are applicable to N-terminal sequencing of isolated proteins. In the illustrative example below, NH2-terminal sequencing was carried out using an Applied Biosystems model 470A gas-phase sequencer which had been modified to eliminate the vacuum system. The Applied Biosystems 02NVAC program was employed, using reagents and solvents supplied by the manufacturer. The PTH-amino acid derivatives which were formed in the instrument by automatic conversion with 25% aqueous trifluoroacetic acid were identified using reverse-phase HPLC. The HPLC system consisted of a Waters WISP sample injector, two Beckman model 112 pumps, a Beckman model 421 controller, an Altex 4.6 mm × 15 cm Ultrasphere-ODS column, two Beckman model 160 detectors in tandem, set to 254 nm and 313 nm, respectively, a Kipp and Zonen two channel recorder and a Spectra-Physics model SP4100 computing integrator. PTH-amino acids were eluted with a gradient of acetonitrile:-methanol (1:1) in 25 mM sodium acetate. pH 4.25.

C.9. Hosts Exemplified

Host strains used in cloning and expression herein are as follows:

For cloning and sequencing, and for expression of construction under control of most bacterial promoters, *E. coli* strain MM294 (supra), Talmadqe K., et al. *Gene* (1980) 12:235; Meselson, M., et al, *Nature* (1968) 217;1110, was used as the host. For expression under control of the $P_LN_{RBS}$ promoter, *E. coli* strain K12 MC1000 lambda lysogen, $N_7N_{53}cI857SusP_{80}$, ATCC 39531 (hereinafter sometimes referred to as MC1000-39531) is used.

For M13 phage recombinants, *E. coli* strains susceptible to phage infection, such as *E. coli* K12 strain DG98 are employed. The DG98 strain has been deposited with ATCC and has accession number 39768.

D. Examples

The following examples are intended to illustrate the invention. Constructions of typical expression vectors for both soluble forms of previously insoluble proteins are illustrated, along with results of transformation with these vectors.

D.1. Construction of Source Vectors for Control Sequences pSYC1089 contains the phoA promoter, leader and coding sequence with a modification to provide a NarI site at the C-terminal end of the leader sequence, followed by the B. thurinoiensis positive retroregulator. The construction of this plasmid, which was used in further vector construction is shown in FIG. 2.

pSYC997: PhoA Promoter and Leader, Modified to Contain NarI Site plasmid pEG247, a 25 kb plasmid containing the 2.6 kb phoA structural gene as a HindIII/XhoI fragment was used as a source of the phoA gene. This plasmid was obtained from M. Casadaban and was constructed in a manner analogous to that set forth in Groisman, E. A., et al, *Proc Natl Acad Sci (USA)* (19B4) 81:1840–1843. Indeed, by applying the procedures set forth in the foregoing reference, the phoA gene may be conveniently cloned into any desirable backbone vector.

The HindIII/XhoI 2.6 kb fragment from pEG247 was purified and cloned into pUC18, a 2,7 kb plasmid containing an ampicillin resistance marker and a polylinker permitting convenient insertion of desired sequences. PUC18 was digested with HindIII/SalI, and the linear vector ligated with the isolated phoA fragment. The ligation mixture was used to transform *E. coli* DG99, a strain comparable to *E. coli* JM103 or JM105, to $Amp^R$, and the construction of the intermediate plasmid pSYC991 in successful transformants, which had been screened for inserts into pUC18, was verified.

pSYC997 which contains the desired NarI modification was prepared from pSYC991 by site-directed mutagenesis. The PvuII/PvuII 770 base pair fragment was obtained from pSYC991. It includes a portion of the phoA promoter and the upstream N-terminal sequences of the mature alkaline phosphatase, and thus, also, the entire leader sequence. This fragment was ligated into the SmaI site of M13mp11 and single stranded phage was prepared as template for the mutagenesis. In the mutagenesis, the synthetic 26-mer, 5'-TTCTGGTGTC$\overline{GGCGCC}$TTTGTCACAG-
-3'

(the superscript line shows the NarI site) was used as primer and probe. The mutagenized phage particles were then used to prepare RF-DNA as a source for the desired leader sequence containing the NarI site.

pSYC1015: $Cm^R$ Marker Backbone Vector pSYC1015 which provides chloramphenicol resistance, a replica, and suitable restriction sites in the phoA gene, is also constructed from pSYC991. pSYC991 was first digested with HindIII/BamHI, and the approximately 2.6 kb fragment containing the phoA gene was purified and ligated with the purified 3.65 kb vector fragment from HindIII/BamHI-digested pACYC184. pACYC184 is available from ATCC and contains the chloramphenicol gene (Cm$^R$), a bacterial replicon, and HindIII and BamHI sites in the tetracycline resistance gene. The ligation mixture was used to transform *E. coli* MM294 to Cm$^R$, and the construction of pSYC1015 was verified by restriction analysis and sequencing.

Additional phoA-Containing Intermediates

Two additional intermediate plasmids, pSYC1052 and pSYC1078, were constructed, as shown in FIG. 2, in order :o provide a suitable host vector for the *B. thuringiensis* positive retroregulator.

pSYC1052 was constructed by ligating the purified small HindIII/BssHII fragment containing the phoA promoter and NarI site from modified leader pSYC997 into HindIII/BssHII-digested pSYC1015, which has, thus, the unmodified phoA sequences deleted. The resulting vector pSYC1052 was confirmed in *E. coli* transformants to $Cm^R$.

pSYC1078 is a modified form of pSYC1052 with the BamHI site in front of the phoA promoter deleted. In order to delete this BamHI site, pSYC1052 was subjected to partial BamHI digestion, filled in using DNA polymerase I (Klenow) in the presence of the four dNTPs, and religated under blunt-end conditions. The desired resulting plasmid, now containing a unique BamHI site just 3' of the phoA gene, was confirmed after screening successful $Cm^R$ transformants.

pHCW701: Source of the Retroregulator

The ability of the 3' sequences of the gene encoding crystal protein from *B. thurinoiensis* (the cry gene) to enhance the expression of upstream coding sequences are characterized by a DNA sequence which transcribes to a corresponding RNA transcript capable of forming a stem and loop structure having a cytosine-guanine residue content of about 43%. When ligated about 30–300 nucleotides from the 3' end of the gene, a positive retroregulatory effect is shown on the gene expression. The positive retroregulator was prepared as a 400 bp EcoRI/BamHI restriction fragment, which was blunt-ended and ligated into pLW1, an expression vector for interleukin-2.

(pLW1 is a pRBR322 derivative containing a replicon effective in *E. coli*, a $Tet^R$ gene, the *E. coli* trp promoter, ribosome binding fragment and a 706 bp HindIII/PstI DNA fragment which includes the gene for human IL-2, pLW1 has been deposited with ATCC under the terms of the Budapest Treaty and has accession no. 39405.)

pHCW701 was completed by blunt-ending the 400 bp EcoRI/BamHI fragment containing the positive retroregulator of the cry gene with Klenow and the four dNTPs, and ligating the blunt-ended fragment using T4 ligase and ATP into StuI-digested plasmid pLW1 . Two possible orientations of insert can result, which are easily distinguishable by restriction analysis. The desired plasmid, designated pHCW701, has therecreated BamHI site closer to the 3' end of the IL-2 gene. This plasmid was deposited with ATCC under the terms of the Budapest Treaty and has accession no. 39757.

Completion of pSYC1089

To complete pSYC1089, pHCW701 was digested with EcoRI, filled in using Klenow and the four dNTPs, then digested with BamHI, and the 400 bp fragment containing the positive retroregulator recovered. pSYC1078 was digested with AvaI, filled in with Klenow and the four dNTPs, and then digested with BamHI. The ligation s Transformed into *E. coli* MM294 and the construction of the desired plasmid pSYC1089, a 5.5 kb plasmid conferring $Cm^R$, was confirmed. PSYC1089 contains the sequences for the phoA promoter and leader (with NarI site) sequence and structural gene immediately upstream of a BamHI site, followed by the positive retroregulator sequences of the cry gene.

D.2. Construction of Ricin A Expression Vectors 0

The ricin A coding sequences were obtained from pRA123, more specifically, an M13 subclone of pRA123, described below, and pRAT1. PRA123 was deposited With ATCC 17 Aug. 1984 and has accession no. 39799. The construction of pRAT1 from pRA123 is described extensively in U.S. Ser. No. 653,515 filed 20 Sept. 1984, assigned to the herein assignee and incorporated herein by reference. Briefly, pRA123, which contains the entire ricin A coding sequence (see FIG. 8), was modified to provide this sequence as a HindIII/BamHI cassette with a termination codon in the proper position after amino acid 265, and with a start codon in position immediately preceding the mature sequence. PRA123 was digested with BamHI and the approximately 896 bp BamHI/BamHI fragment was isolated and subcloned into M13mp18 in an anti-sense orientation relative to the lac promoter in the M13 vector. The phage single stranded DNA was subjected to two stages of primer directed mutagenesis using as primers, the sequence:

5'-CACAGTTTTAATTGCTTATAAGG-3', which places the TAA termination codon in proper reading frame at the terminus of the ser-gln-phe C-terminus of the ricin A chain followed by:

5'-CTTTCACATTAGAGAAGCTTAT-
GATATTCCCCAAAC-3', which places the desired HindIII/ATG start codon diad immediately upstream of the N-terminal ile-phe-pro-lys sequence of ricin A. The modified phage were identified after each mutagenesis using the appropriate above primers as probes. The desired constructs were then double digested with HindIII and BamHI and the appropriate ricin A coding fragment isolated. PRAT1 was completed by ligation of the HindIII/BamHI fragment with HindIII/BamHI digested pTRp3. pTRp3 is a pBR322 based vector containing the trp promoter with a downstream HindIII site; pTRp3 was deposited with ATCC 18 Dec. 1984, and has accession no. 39946.

Three expression vectors were constructed. Two were vectors having the ricin A sequences in reading frame with leader and were constructed using pRAT1 and modified M13 subclones of pRA123 generally as shown in FIG. 3. A third expression vector typical of those of the invention, pRAP229 was constructed using coding sequences derived entirely from pRAT1 as shown in FIG. 4.

For the two in-frame vectors, PRAP218 and pRAP2210, the constructions employed a three-way ligation between (1) the large NarI/BamHI replicon-containing fragment of pSYC1089 which provides, in order, *B. thurinoiensis* -positive retroregulator sequences, the chloramphenicol resistance marker, a compatible replicon, and the phoA promoter and leader sequences; (2) ClaI/BamHI-digested PRAT1 which provides a 500 bp fragment encoding the C-terminal portion of ricin A properly terminated; and (3) a 350 bp fragment upstream of the ClaI site in RF-DNA of appropriately modified M13/pRA123 subclones which contain the amino terminal encoding portion of ricin A.

For pRAP218, this latter fragment was derived from an M13/pRA123 subclone modified by site specific mutagenesis using:

5'-CATTAGAGGATAACTGCGCATTCCCCAAAC-3' as primer. This places an MstI site at the N-terminus of the ricin A coding sequence. The desired 350 bp MstI/ClaI fragment from the modified pRA123, was ligated in three-way ligation mixture with ClaI/BamHI-digested pRAT1 and NarI/BamHI-digested pSYC1089 after the NarI site had been blunt-ended using *E. coli* DNA polymerase I (Klenow) in the presence of dCTP and dGTP. The resulting fusion contains an N-terminal alanine in place of the isoleucine of the ricin A sequence directly ligated in reading frame with the codon for the C-terminal alanine of the leader as shown in FIG. 5a.

pRAP2210 was constructed analogously except that the N-terminal sequences were provided as a 350 bp BglII/ClaI fragment from an M13 subclone modified using:

BglII
5'-CATTAGAGGATAACAAGATCTTCCCCAAAC-3' as primer, which places a BglII site at the ricin A N-terminus. The BglII cleavage site was first partially repaired using dTTp, dATP and dGTp as substrates in the presence of Klenow and ligated in a mixture with ClaI/BamHI-digested pRAT1 and NarI/BamHI-digested pSYCIO89 after the NarI cleavage site of the vector fragment had been partially repaired using dCTp in the presence of Klenow. The resulting ligation gave the sequence shown in FIG. 5*b* wherein the correct fusion contains the native N-terminal isoleucine codon fused in reading frame to the C-terminal alanine of the leader.

The out-of-frame plasmid of the invention, pRAP229, was obtained by a similar three-way ligation except that the N-terminal sequence was provided by an approximately 350 bp ClaI/ClaI fragment from pRAT1 and the NarI site of the vector fragment was unrepaired. It is clear that the ricin A sequences could also have been, and might preferably be, prepared as a ClaI(partial)-/BamHI-excised fragment from pRAT1. The resulting fusion (1) retains the start codon of the ricin A chain preceding the isoleucine residue; (2) is separated by 7 bp and thus out of reading frame relative to the leader sequence; (3) extends the phoA leader by the tripeptide Ile-Ser-Leu; and (4) allows for termination of the leader sequence at a TGA codon out of frame with, but proximal to, the start codon of rican A The sequence at the pRAP229 fusion is shown in FIG. 5*c*. PRAP229 was deposited at ATCC on 8 Mar. 1985 and has accession no. 53408.

D.3. production of Ricin A in *E. coli* pRAP218, pRAP2210, and pRAP229 were transformed into *E. coli* MM294 and the transformed cultures were grown under conditions similar to those described by Michaelis, et al, J Bact (1983) 154:356–365. The cells were induced by lowering the exogenous phosphate concentration and maintaining the cultures for 16–17 hr.

The cells were harvested, and whole cell extracts prepared by sonication in the absence of detergent were assayed for expression using Western blot employing rabbit antisera to native ricin A. The results are shown in FIG. 6 for pRAP218 and for pRAP229. (The results for pRAP2210 were exactly analogous to those for pRAP218.)

In FIG. 6, lanes 1 and 2 represent native and recombinant ricin, respectively. (The recombinant ricin d using pRAL6-transformed *E. coli* MM294, and was produced using pRAL6-transformed *E. coli* MM294, and the whole cell extract prepared by sonication was subjected to analysis. PRAL6 (ATCC #39833) is a plasmid analogous to pRAT1, except that the ricin A sequences are operably linked to the $P_L$ promoter. It is extensively described in copending U.S. Ser. No. 837,583, filed 7 Mar. 1986. incorporated herein by reference.) In lane 1, the two forms of the native protein, $A_1$ and $A_2$, which differ in the extent of glycosylation are clearly apparent. In lane 2, the large smeared spot of recombinant ricin A is an artifact resulting from overloading of the gel; it migrates, however, at the appropriate molecular weight (28 kD) for non-glycosylated rican A. Lanes 3–8 represent extracts of induced pRAP218 cultures. Lane 3, the osmotic shockate shows the absence of ricin A protein in the periplasm, Lane 4, which is a shockate pellet, indicates that the protein resides intracellularly, or at least is associated with cellular structural components. Lanes 5, 6, and 7 are various fractions of the 3 min sonicates indicating a distribution of the protein through the fractions of the sonicate. Lane 5 is the low speed pellet; lane 6 the low speed supernatant; lane 7 the 100,000×g supernatant. Lane 8 corresponds to a 3 min sonication plus SDS to release all protein. Lane 9 is a control showing that uninduced transformants contain no ricin A.

Lanes 10–15 are the corresponding results from *E. coli* transformed with pRAP229. Again, the osmotic shockate (lane 10) contains no ricin A, while the intracellular components show the presence of the ricin A protein. It is important to note that in lane 14, the free ricin A protein is not removed from the supernatant by 100,000×g centrifugation. The presence of ricin A in pellet fractions is due to inefficient extraction of ricin A from membranes or other associated materials.

Estimation of quantities of materials present in non-blotted Coomassie-stained polyacrylamide gels show that for the in-frame plasmids, pRAP218 and pRAP 2210, the production is approximately 1–2% of total cell protein, and that the ricin A is approximately equally distributed between processed (28 kD) and unprocessed (30kD) protein. For pRAP229, however, only molecular weight 28 kD is obtained and this comprises at least 5–6% of total cell protein. Analysis of this purified protein product shows that approximately 33% of the sequenceable protein is N-terminated by methionine; the remainder by isoleucine. (N-Formyl methionine-preceded peptides cannot be sequenced.)

D.4 purification of Ricin A

To obtain sufficient ricin A protein for purification cells were grown in a 10 liter fermenter and induced by depletion of phosphate concentration. The cells were grown in a medium which contained an autoclaved solution of 100 mM ammonium sulfate, 5 mM $KH_2PO_4$, 1 mM sodium citrate, and 1 mM TK-9 which was supplemented with the following sterile additions: 3 mM $MgSO_4$, 5 g/l glucose. 20 mg/l thiamine hydrochloride, 72 μM ferrous sulfate, and 25 mg/l chloramphenicol. Inoculation was at 1 mg dry weight per liter from shake flasks of the transformants grown in a mineral salts/-glucose medium.

After inoculation, the temperature of the fermenter was kept at 37° C. and the pH controlled to 6.8 by addition of KOH and coupled glucose feed. Dissolved oxygen was controlled at 40% of air saturation. Induction occurred upon depletion of the phosphate at an OD of approximately 20. The cells were harvested by centrifugation at low speed approximately 4-5 hr after apparent induction.

Forty grams wet weight of cells were sonicated in the presence of 100 ml buffer X (buffer X contains 0.1 M Tris, pH 8.5; 25 mM EDTA, 0.1% β-mercaptoethanol) containing 0.5 M NaCl. After 30 minutes of sonication, 1 mg of phenyl methyl sulfonyl fluoride (pMSF) in 1 ml DMSO was added, and the sonicated mixture centrifuged for 30 minutes at 12,000×g. Note that the supernatant will still contain components which do not meet the herein defined criteria of solubility, as the centrifugation speed is relatively low.

The supernatant, which was not completely clarified, was loaded onto a column having a hydrophobic matrix, in this example a phenylsepharose (pharmacia, Ltd) column having a bed volume of 200 ml which had been equilibrated with phosphate-buffered saline (pBS), pH 7. Other column materials which are substantially hydrophobic are contemplated to be within the scope of the invention. Such hydrophobic material includes higher alkyl-, aryl-, alkylaryl-, and arylalkyl-substituted sepharoses. The column was chased with 1 bed volume PBS, and then the protein eluted with a 0-50% propylene glycol gradient in PBS. Fractions were assayed by subjecting them to SDS gel electrophoresis and staining with Coomassie blue, using migration of previously authenticated ricin A purified from pRAL6 transformants to identify the desired bands. Recombinant ricin A may be eluted with lower alkyl- ($C_1$-$C_6$) substituted glycols of which ethylene and propylene glycol are examples. Propylene glycol is preferred. Recombinant ricin A eluted from the column at approximately 15% propylene glycol and the ricin A-containing fractions were pooled and diluted 10 times into buffer Y (20 mM sodium acetate, pH 5.5; 1 mM EDTA, 0.1% β-mercaptoethanol) for the succeeding purification steps.

This ricin A was soluble by the criteria herein defined. Control experiments without the use of phenyl sepharose yielded a soluble product, but immunoprecipitable ricin A remained associated with larger fragments which came down in the pellet during centrifugation. In addition, the yield of ricin A defined as soluble is greatly improved using phenyl sepharose as an adsorbent in the purification process.

The pooled fractions were further purified on a carboxymethyl sepharose column having a 200 ml bed volume which had been preequilibrated with buffer Y. Fractions were eluted with a 100–250 mM NaCl gradient in buffer Y, and the fractions were assayed using SDS gel/Coomassie blue staining, as above. The ricin A fractions eluted at approximately 150 mM NaCl and provided ricin A of approximately 95% purity, sufficient for research use.

The pooled ricin A-containing fractions were further purified by diluting ten-fold in buffer X and then applying the pool to a Cibacron Blue F3GA (Blue Trisacryl™, LKB) column. Fractions were eluted in 0–1 M NaCl in buffer X. Ricin A fractions were again identified by SDS gel/Coomassie blue staining, and shown to be eluted at approximately 0.5 M NaCl. These fractions showed a single band on SDS-PAGE. as shown in FIG. 7. FIG. 7 compares gels from the Trisacryl™ fractions with those from the soluble sonicate protein fraction. These fractions were pooled and could be used directly for conjugation to antibody. The material eluting from the Trisacryl™ column was active in the rabbit reticulocyte protein synthesis inhibition assay at approximately the same level as native ricin A (see below).

D.5 Immunotoxins Using Ricin A of the Invention

The pRAP229 products. Purified as above, were used to prepare immunoconjugates with the monoclonal antibody 454A12 an immunoqlobulin specific for the human transferring receptor, and to the anti-breast monoclonal 280D11. Conjugates were prepared by two general methods, using iminothiolane or SPDP as linkers.

To form the conjugates, the procedures described by Bjorn, M.J., et al, *Biochim Biophys Acta* (1984) 790:154–163, were used. Briefly, breast monoclonal antibody 280D11, anti-transferring receptor 454A12 or other desired antibodies were first derivatized with SPDP, and used to form disulfide links to the free cysteine sulfhydryls of ricin A. A 10–20 fold molar excess of SPDP was added to a solution containing 20 mg/ml of antibody ln PBS and incubated at room temperature for 1 hr. and then dialyzed against PBS to remove unreacted SPDP. It was calculated that approximately 2–5 pyridyl-disulfide moieties were introduced into each antibody using this procedure. To complete the conjugation, solutions of ricin A containing 1–2 mg/ml which had been stored in reducing agent in 4° C. was passed over a Sephadex G-25 column equilibrated in PBS to remove the reducing agent, and the ricin A was mixed with derivatized antibody in 2–4 molar excess cytotoxic portion. Conjuqation was confirmed by spectrophotometric determination of released pyridine-2-thiol and by SDS-pAGE.

In an alternative approach, the appropriate antibody was dialyzed against 100 volumes of 100 mM sodium phosphate, pH 8. 1 mM EDTA, (P-EDTA) at 4° C. The dialyzed antibody solution was made 1 mM in 5.5′-dithiobis(2-nitrobenzoic acid) (DTNB), followed by addition of 2.5 equivalents of 2-iminothiolane (10 mM stock in water). The reaction was allowed to proceed for 24 hours at 0"C. The number of thiols introduced by 2-iminothiolane and subsequently blocked by DTNB Was determined by thionitrobenzoate release (extinction coefficient, 13,600/M at 412 nm). Excess 2-iminothiolane and DTNB were removed by dialysis against 3 ×100 volumes P-EDTA at 4° C. The ricin A moiety (>10 mg/ml) was also dialyzed against P-EDTA and the number of free thiols determined spectrophotometrically using DTNB. Coupling was effected using a 1.2 fold excess of ricin A free thiols over antibody blocked thiols, and the reaction monitored at 412 nm. Reaction was complete in 12 hours.

Conjugates were prepared using the soluble ricin A of the invention as well as using recombinant (pRAL6) ricin A, which is soluble only in detergent, and native ricin A. Immunotoxins can be tested in in vitro and in vivo cytotoxicity assays as described below.

For the assays, some of the immunotoxins were first purified. It was not possible to purify the immunoconjugates resulting from recombinant (pRAL6) ricin A. which were also soluble only in detergent. The conjugates of soluble ricin A of the invention and of native ricin A were first purified using a combination of fractionation on Blue Trisacryl™ and sizing on ACA-44. The original mixture, which contains free antibody, free ricin A. and the conjugate was first subjected to treatment with Blue Trisacryl ™, which has an affinity for both ricin A and its conjugates. The mixture eluted from the column containing ricin A and ricin A conjugate was then subjected to size fractionation using ACA-44 to separate the unconjugated ricin A. The resulting conjugates were approximately >95% pure, when used in the assays below.

The in vitro assay followed the protocol set forth in Bjorn, et al (supra). In a typical protocol. human breast tumor cells (MCF-7) were seeded in 8 ml glass vials and dilutions of the immunoconjugates were added. Following incubation for 22 hrs at 37° C. the medium was removed and replaced with 0.5 ml medium lacking unlabeled methionine, but supplemented with 1 μCi of $^{35}$S methionine. Following a 2-hr pulse, the medium was aspirated, the monolayer was washed twice with 10% trichloroacetic acid containing 1 mg/ml methionine and the vials were dried. Following the addition of 3 ml of 4a20 ™ scintillation fluid (Research Products International Corp.) containing 20% (v/v) Triton X-100, the vials were counted. Toxicity was expressed as the concentration of protein required to inhibit protein synthesis by 50% (TCID50).

In the in vivo assay, animals which had been implanted with tumors are used as subjects, and conjugates are injected to evaluate their effect on tumor growth. The results can be computed as % growth of tumors in experimental animals as compared to control.

Ricin A and its conjugates were also tested for toxicity by injection IV into Balb/C mice. LD$_{50}$ values were determined for conjugates both of the recombinant soluble ricin A of the invention and for native ricin A. Toxicity could not be determined for conjugates prepared from the insoluble recombinant (pRAL6) ricin A since these conjugates were unavailable in sufficient amounts, could not be purified and contained detergents.

The results of the tests with regard to enzymatic activity as well as of the foregoing in vitro and toxicity tests are shown below in Table 1.

As shown in Table 1, the enzymatic activity refers to the amount of ricin A in ng/ml required to give 50% inhibition of protein synthesis in the commercially available rabbit reticulocyte in vitro translation system.

Toxicity was computed as LD $_{50}$ values obtained from a single injection IV of ricin A into Balb/C mice.

Cytoxocity was measured in vitro using immunotoxins with the ricin A proteins prepared as described above. Controls using either unconjugated native ricin A or pRAP229 ricin A showed cytotoxicity of about 20 mM.

The assay procedures were as described above. MCF-7 were used as sensitive cell lines, and the results tabulated are the concentrations in nM of the conjugate able to elicit 50% killing of the sensitive cell line. Control non-sensitive cell lines, for example. CC95 typically showed TCID$_{50}$ values Wit h the immunoconjugates of this assay of more than 100 nM.

TABLE 1

Representative Biological Activity
Comparison of Ricin A from pRAP229 and Native Ricin A

|  | native ricin A | pRAP229 ricin A |
| --- | --- | --- |
| Enzymatic | 1.76 ng/ml | 0.76 ng/ml |
| Activity | 1.78 ng/ml | 1.58 ng/ml |

TABLE 1-continued

Representative Biological Activity
Comparison of Ricin A from pRAP229 and Native Ricin A

|  | native ricin A | pRAP229 ricin A |
| --- | --- | --- |
| Toxicity LD$_{50}$ | 350 μg | 340 μg |
| Cytotoxicity of Immunoconjugates against MCF-7 |  |  |
| Mab 454A12 | 0.01 nM | 0.02 nM |
| Mab 280D11 | 0.1 nM | 0.4 nM |
|  | 0.08 nM |  |

The soluble pRAP229 ricin A of the invention shows comparable properties within experimental error to those of native ricin A, including enzymatic activity and formation of specifically cytotoxic conjugates. preliminary results in in vivo assays suggest that the ability of immunoconjugates of native ricin A and of pRAP229 ricin A to inhibit tumor growth is also comparable. The materials listed below were deposited with the American Type Culture Collection, Rockville, MD, U.S.A. (ATCC). The deposits were made under the provisions of the Budapest Treaty on the INternational REcognition of the Deposited Microorganisms for the Purposes of Patent Procedure and Regulations thereunder (Budapest Treaty). Maintenance of a viable culture is assured for 30 years from date of deposit. The organism will be made available by ATCC under the terms of the Budapest Treaty, and subject to an agreement between applicants and ATCC which assures unrestricted availability upon issuance of the pertinent U.S. Patent. Availability of the deposited strain is not to be construed as a license to practice the invention and contravention of the rights granted under the authority of any Government in accordance with its patent laws.

| Plasmid | Deposit Date | CMCC# | ATCC# |
| --- | --- | --- | --- |
| pRA123 | 17 August 1984 | 2108 | 39799 |
| pRAL6 | 4 September 1984 | 2114 | 39833 |
| E. coli K12DG98 | 13 July 1984 | 1965 | 39768 |
| pRAP229 | 8 March 1985 | 2218 | 53408 |

We claim:

1. A system for production of a soluble, biologically active, heterologous protein in procaryotic hosts, which system comprises DNA having the coding sequence for a ricin A protein initiated by an ATG initiation codon, said initiated coding sequence operably linked to, and out of reading frame with, the terminated leader DNA sequence encoding bacterial alkaline phosphatase (phoA).

2. The system of claim 1, which further includes a promoter operable in bacterial hosts.

3. The system of claim 2, wherein the bacterial promoter is the phoA promoter.

4. The system of claim 1, which further includes a positive retroregulator compatible with baterial hosts.

5. The system of claim 4, wherein the positive retroregulator is a DNA sequence isolated from a gene of the crystal proteins of B. thuringiensis.

6. The system of claim 1, which is located on a bacterial expression vector containing a replicon and a selectable marker.

7. Recombinant procaryatic host cells transformed with the vector of claim 6.

8. A method for producinq-a soluble. biologically active, recombinant ricin A protein which comprises culturing the cells of claim 7.

* * * * *